(12) United States Patent
Bogdanowicz et al.

(10) Patent No.: US 8,717,570 B2
(45) Date of Patent: May 6, 2014

(54) METHOD FOR DETERMINING THE ACTIVE DOPING CONCENTRATION OF A DOPED SEMICONDUCTOR REGION

(71) Applicants: IMEC, Leuven (BE); Katholieke Universiteit Leuven, Leuven (BE)

(72) Inventors: Janusz Bogdanowicz, Leuven (BE); Trudo Clarysse, Leuven (BE); Wilfried Vandervorst, Leuven (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 13/689,473

(22) Filed: Nov. 29, 2012

(65) Prior Publication Data
US 2013/0155409 A1    Jun. 20, 2013

Related U.S. Application Data

(63) Continuation of application No. PCT/EP2011/059258, filed on Jun. 6, 2011.

(60) Provisional application No. 61/351,705, filed on Jun. 4, 2010, provisional application No. 61/487,162, filed on May 17, 2011.

(51) Int. Cl.
*G01N 21/55* (2006.01)

(52) U.S. Cl.
USPC .......................................... 356/445; 356/448

(58) Field of Classification Search
USPC ......... 356/445–448, 432, 435, 601, 609, 369, 356/72, 492, 493, 496, 503, 504, 36, 356/237.1–237.6, 502, 498; 250/201.2, 250/559.45, 559.46, 307, 308, 310, 201.1, 250/559.4
See application file for complete search history.

(56) References Cited

U.S. PATENT DOCUMENTS

2008/0036998 A1* 2/2008 Salnik et al. .................... 356/36

FOREIGN PATENT DOCUMENTS

EP          2139033 A2    12/2009

OTHER PUBLICATIONS

L. Nicolaides et al., "Non-destructive analysis of ultrashallow junctions using thermal wave technology", Review of Scientific Instruments, vol. 74, No. 1, Jan. 2003, pp. 586-588.
E. Rosseel et al., "Study of submelt laser induced junction nonuniformities using Therma-Probe", J. Vac. Sci. Technol. B, vol. 28, No. 1, Mar. 1, 2010, pp. C1C21-C1C26.
International Search Report for International application No. PCT/EP2011/059258 dated Aug. 22, 2011 by European Patent Office.
D.B.M. Klaassen et al., "Unified Apparent Bandgap Narrowing in *n*- and *p*- Type Silicon", Solid-State Electronics, vol. 35, No. 2, 1992, pp. 125-129.

(Continued)

*Primary Examiner* — Tri T Ton
(74) *Attorney, Agent, or Firm* — Knobbe, Martens, Olson & Bear LLP

(57) ABSTRACT

A method and system for optically determining a substantially fully activated doping profile are disclosed. The substantially fully activated doping profile is characterized by a set of physical parameters. In one aspect, the method includes obtaining a sample comprising a fully activated doping profile and a reference, and obtaining photomodulated reflectance (PMOR) offset curve measurement data and DC reflectance measurement data for the sample including the fully activated doping profile and for the reference. The method also includes determining values for the set of physical parameters of the doping profile based on both the photomodulated reflectance offset curve measurements and the DC reflectance measurements.

10 Claims, 9 Drawing Sheets

(56) References Cited

OTHER PUBLICATIONS

T. Clarysse et al., "On the analysis of the activation mechanisms of sub-melt laser anneals", Material Science and Engineering B 154-155, 2008, pp. 24-30.

J. Bogdanowicz et al., "Nondestructive extraction of junction depths of active doping profiles from photomodulated optical reflectance offset curves", Journal of Vacuum Science and Technology B, vol. 28, No. 1, Jan./Feb. 2010, pp. C1C1-C1C7.

J. Bogdanowicz, "Fundamental Study of Photomodulated Optical Reflectance towards Non-Destructive Carrier Profiling in Silicon", PhD. Thesis, Katholieke Universiteit Leuven, Arenberg Doctoral School of Science, Engineering & Technology, Faculty of Science, Department of Physics and Astronomy, May 2011.

Pierre Eyben, "Scanning spreading resistance microscopy: High resolution two-dimensional carrier profiling of semiconductor structures", PhD. Thesis, Katholieke Universiteit Leuven, Faculteit Toegepaste Wetenschappen, Dec. 2004.

A. Salnick et al., "Quantitative photothermal characterization of ion-implanted layers in Si", Journal of Applied Physics, vol. 91, No. 5, Mar. 1, 2002, pp. 2874-2881.

A. Salnick et al., "Dynamic of the plasma and thermal waves in surface-modified semiconductor (invited)", Review of Scientific Instruments, vol. 74, No. 1, Jan. 2003, pp. 545-549.

C. Christofides et al., "Photothermal reflectance investigation of processed silicon. I. Room-temperature study of the induced damage and of the annealing kinetics of defects in ion-implanted wafers", Journal of Applied Physics, vol. 67, No. 6, Mar. 15, 1990, pp. 2815-2821.

T. Clarysse et al., "Towards nondestructive carrier depth profiling", Journal of Vacuum Science and Technology B, vol. 24, No. 3, May/Jun. 2006, pp. 1139-1146.

J. Bogdanowicz et al., "Advances in optical carrier profiling through high-frequency modulated optical reflectance", Journal of Vacuum Science and Technology B, vol. 26, No. 1, Jan./Feb. 2008, pp. 310-316.

F. Dortu et al., "Extracting active dopant profile information from carrier illumination power curves", Journal of Vacuum Science and Technology B, vol. 24, No. 1, Jan./Feb. 2006, pp. 375-380.

Fabian Dortu, "Low Frequency Modulated Optical Reflectance for the One-Dimensional Characterization of Ultra Shallow Junctions", PhD. Thesis, Katholieke Universiteit Leuven, Faculteit Toegepaste Wetenschappen, May 2009.

T. Yasuda et al., "Optical-standard surfaces of single-crystal silicon for calibrating ellipsometers and reflectometers", Applied Optics, vol. 33, No. 31, Nov. 1, 1994, pp. 7435-7438.

T. Noda et al., "Analysis of Dopant Diffusion and Defect Evolution during sub-millisecond Non-melt Laser Annealing based on an Atomistic Kinetic Monte Carlo Approach", International Electron Device Meeting (IEDM) conference proceedings 2006, Dec. 11-13, 2006, San Francisco, CA, US.

J. Bogdanowicz et al., "Electrothermal theory of photomodulated optical reflectance on active doping profiles in silicon", Journal of Applied Physics 108, 2010, pp. 104908-1-104908-25.

Michael T. Heath, "Scientific Computing; Chapter 6, Optimization", MacGraw-Hill, 1997, pp. 179-213.

\* cited by examiner

US 8,717,570 B2

METHOD FOR DETERMINING THE ACTIVE DOPING CONCENTRATION OF A DOPED SEMICONDUCTOR REGION

CROSS REFERENCE TO RELATED APPLICATIONS

This application is a continuation of PCT Application No. PCT/EP2011/059258, filed Jun. 6, 2011, which claims priority under 35 U.S.C. §119(e) to U.S. provisional patent applications 61/351,705 filed on Jun. 4, 2010 and 61/487,162 filed on May 17, 2011. Each of the above applications is incorporated herein by reference in its entirety.

BACKGROUND OF THE INVENTION

1. Field of the Invention

The disclosed technology relates to the field of characterization of doped semiconductors, and more particularly non-destructive optical measurement techniques for determining the active doping concentration profile of a semiconductor region.

2. Description of the Related Technology

The ITRS roadmap highlights the precise characterization of ultra-shallow junctions, formed by shallow doping of semiconductor regions, as one of the top challenges for sub-32 nm Si-CMOS technologies. Such a junction is typically characterized by a maximum active doping level N and a junction depth $X_j$ and an abruptness S.

The accurate measurement of free carrier profiles in ultra-shallow junctions (USJ), such as the source and drain extension regions, is one of the major challenges of metrology in modern silicon Complementary metal-oxide-semiconductor technology. The used physical and electrical analytical techniques for determining the maximum doping level and junction depth, such as secondary ion mass spectrometry (SIMS), spreading resistance profiling (SRP), four point probe (FPP), or alternative candidates, such as scanning spreading resistance microscopy (SSRM) allow an accurate determination of this junction depth $X_j$. However these characterization techniques are destructive and quite slow, e.g. as samples have to be prepared, and therefore prevent any in-line measurement. There is still a clear absence of an accurate, fast, non-destructive technique.

Photomodulated optical reflectance (PMOR) is a widely used non-destructive and contactless technique to characterize in a qualitative way the doping profile of such a doped semiconductor region. It is a fully optical, hence non-contact, pump-probe technique. During measurement, a modulated-power pump laser is directed towards the doped semiconductor region to modify the refractive index profile thereof. This refractive index profile can be modified through generation of excess carriers in the sample, also known as the Drude effect, and/or by temperature effects of the sample under study. Simultaneously a probe laser is directed to this doped semiconductor region where it will be reflected depending on the refractive index profile. By coupling the reflected probe laser signal to a lock-in amplifier, only the variations in the reflectivity of the doped semiconductor sample induced by the modulated pump laser are measured. The probe laser thus measures, via reflection, the changes in refractive index induced by the pump laser.

PMOR is commonly used for monitoring implant dose in as-implanted (i.e. unannealed) silicon wafers, and hence has been the subject of much investigation in this field. On such as-implanted profiles, the variation in refractive index is due to the large increase in the temperature in the illuminated sample (dominant thermal component). This technique has also been studied extensively on box-like active doping profiles as obtained by chemical vapor deposition (CVD), where the measured signals are due mostly to the pump-generated excess carriers with only a weak contribution due to a mild increase in temperature (dominant plasma component).

An example of such PMOR technique is the Therma-Probe® technique (TP) described in "Non-destructive analysis of ultra shallow junctions using thermal wave technology" by Lena Nicolaides et al. in Review of Scientific Instruments, volume 74, number 1, January 2003. The TP technique is a high-modulation-frequency implementation of the PMOR technique.

SUMMARY OF CERTAIN INVENTIVE ASPECTS

Certain inventive aspects relate to non-destructive methods and systems for determining a fully activated doping profile of a doped semiconductor region.

It is an advantage of certain inventive aspects that a user friendly and easy to operate method may be applied for determining the active dopant profile of a semiconductor substrate in a short measurement time.

It is an advantage of certain inventive aspects that a complete active doping profile can be determined or reconstructed from an optical measurement on the doping profile. The active doping profile may be any arbitrary doping profile.

In one aspect, PMOR can be used for determining activated implantation profiles whereby PMOR signals are due to a subtle balance between the plasma and thermal components. In particular, it is an advantage of one aspect that the combined information contained in the PMOR offset curves, wherein the PMOR signal is measured as a function of pump-probe beam separation, and in the time-independent (DC) reflectance, is combined and is sufficient to reconstruct the underlying free carrier profile.

It is an advantage of at least some inventive aspects to provide a method or system to extract the junction depth whereby the extracted junction depth is in very good correlation with the junction depth obtained by SIMS.

It is an advantage of at least some inventive aspects to provide a method or system to extract this junction depth with sub-nm reproducibility for depths ranging from about 15 to 30 nm.

It is an advantage of at least some inventive aspects to provide a method or system to extract the peak doping concentration of a doping profile.

It is an advantage of at least some inventive aspects that a complete active doping profile can be measured for samples having a high doping concentration without substantially destroying the samples.

It is an advantage of at least some inventive aspects that carrier profiles in ultra shallow junctions can be determined non-destructively, i.e. without sample preparation.

It is an advantage of at least some inventive aspects that doping incorporation may be monitored at key points in the process flow and thus leading to an enhanced product quality.

It is an advantage of at least some inventive aspects that a method for determining the active dopant profile may be applied in-line, i.e. in the production process environment.

It is an advantage of at least some inventive aspects that a unique solution may be determined for the active doping profile based on an optical measurement of the active doping profile.

It is an advantage of at least some inventive aspects that an unknown arbitrary doping profile may be reconstructed from an optical measurement in a fast and flexible way while no prior assumptions need to be made about the doping concentration or the junction depth.

It is an advantage of at least some inventive aspects that photomodulated optical measurement techniques for determining the active doping concentration profile of a semiconductor region are provided, as well as devices and software for carrying out the techniques.

It is an advantage of at least some inventive aspects that methods and systems as well as software is provided for independent extraction of the peak dopant concentration and/or the junction depth and/or the abruptness in a particular semiconductor substrate.

It is an advantage of at least some inventive aspects that measurement of activated implantation profiles can be measured in a direct manner, requiring little or no sample preparation.

It is an advantage of at least some inventive aspects that reconstruction of underlying free carrier profiles for activated implantation profiles can be reconstructed, based on a combination of PMOR signals and simultaneously measured DC probe reflectance of the sample. The results are in good agreement with secondary ion mass spectrometry and scanning spreading resistance microscopy measurements with an average accuracy of about 3 nm (for the junction depth).

It is an advantage of at least some inventive aspects that complete dopant profiles can be reconstructed, rather than that only a determination of the junction depths can be obtained.

It is an advantage of at least some inventive aspects that use is made of a DC component sensitive at high dopant concentrations (such as for example present in modern ultra shallow junctions, wherein active doping concentrations can be up to $10^{20}$ cm$^{-3}$ or higher) and an AC component sensitive for lower concentrations for obtaining a good sensitivity for the full dopant concentration profile.

In one aspect there is a method for optically determining a substantially fully activated doping profile, the substantially fully activated doping profile being characterized by a set of physical parameters, the method comprising: obtaining a sample comprising a fully activated doping profile and a reference, obtaining photomodulated reflectance (PMOR) offset curve measurement data and DC reflectance measurement data for the sample comprising the fully activated doping profile and for the reference, and determining values for the set of physical parameters of the doping profile based on both the photomodulated reflectance offset curve measurements and the DC reflectance measurements.

Obtaining photomodulated reflectance offset curve measurement data and DC reflectance measurement data may be done by performing a photomodulated reflectance offset curve measurement and by performing a DC reflectance measurement.

With DC reflectance measurement, there is meant a time-independent reflectance measurement or reflectance measurement allowing determination of the overall reflectance of the sample.

Obtaining photomodulated reflectance offset curve measurement data and DC reflectance measurement data may be obtaining data recorded using the same measurement setup.

Obtaining photomodulated reflectance offset curve measurement data and DC reflectance measurement data may be obtaining data recorded substantially simultaneous or simultaneous.

The method typically also comprises selecting a predetermined profile shape for fully activated doping profile defined by the set of physical parameters, whereby determining values for the set of physical parameters comprises determining values for the set of physical parameters defining the predetermined profile shape.

Determining the set of physical parameters of the doping profile may comprise determining a surface excess carrier concentration $\Delta N_{sub}$ and excess temperature $\Delta T_{surf}$ from the photomodulated reflectance offset curve measurement data obtained for the reference and determining a reflectance $R_0$ from the DC measurement data obtained for the reference.

Determining the set of physical parameters of the doping profile may comprise determining from the photomodulated reflectance offset curve measurement data on the sample and from the DC reflectance measurement on the sample one, more or preferably all of a junction depth $X_j$, an active doping concentration $N_{act}$ and a profile abruptness or backside slope $S_{act}$.

In one aspect, there is an optical measurement method for determining a substantially fully activated doping profile, the substantially fully activated doping profile being characterized by a set of physical parameters, the method comprising a) providing a sample comprising the fully activated doping profile and a reference, b) performing a sample measurement, the sample measurement comprising determining sample parameters from a photomodulated reflectance measurement on the sample, c) performing a reference measurement, the reference measurement comprising determining substrate parameters from a photomodulated reflectance measurement on the reference, and d) extracting the set of physical parameters from the substrate parameters and the sample parameters;

With reference is meant a part of the sample or another sample which is free of dopants, but which has undergone the same process steps, i.e. for example activation step and pre-amorphization step, except for the doping incorporation step as the sample with the substantially fully activated doping concentration profile. It is thus important that for both the sample and the reference the same activation process is performed whereas for the reference no dopants will be activated since the reference is free of dopants, and whereas for the sample substantially all dopants will be activated. If the sample underwent for example a pre-amorphization implant and a subsequent annealing step, the reference (which is free of dopants) will also undergo a pre-amorphization implant and a subsequent annealing step with the same parameters as used for the sample.

A sample may be provided comprising a doped part (the doped part comprising the substantially fully activated doping profile). The sample may comprise also the reference, whereby the reference may be an undoped part, i.e. free of dopants.

The substantially fully active doping profile may be characterized by a set of physical parameters. The set of physical parameters may comprise a junction depth $X_j$, an active doping concentration $N_{act}$, a profile backside slope $S_{act}$, a surface active doping concentration $N_{surf}$. In general a doping profile may be characterized by an arbitrary functional dopant ($X_j$, $N_{act}$, $S_{act}$, $N_{surf}$, . . . ). Dependent on the number of independent inputs ($n_{input}$) gathered in addition to the photomodulated reflectance (PMOR) measurement, see later, the number of physical parameters that can be determined is at least $1 + n_{input}$.

A doping profile may for example be characterized by a Gaussian profile:

$$N(z) = N_0 \exp(-(z-\Delta)^2/W^2)$$

The Gaussian profile may for example be centered at z=0 (i.e. $\Delta=0$), which means the peak concentration of the doping concentration profile is positioned at the surface. In this case two physical parameters need to be determined ($N_0$ and W) and therefore one independent measurement (for example a PMOR DC measurement) is needed on top of the basic PMOR measurement, see later.

A doping profile may for example be characterized by a Lorentzian function $$N(z) = N_0 \frac{1}{1 + (z - \Delta)^2 / W^2}$$

The Lorentzian profile may for example be centered at z=0 (i.e. $\Delta$=0). In this case two physical parameters need to be determined ($N_0$ and W) and therefore one independent measurement (for example a PMOR DC measurement) is needed on top of the basic PMOR measurement (see later).

A doping concentration profile may for example be characterized by a Complementary Error function.

$$N(z) = \frac{2N_0}{\sqrt{\pi}} \int_z^{+\infty} \exp(-(t-\Delta)^2/W^2) \, dt$$

The Complementary Error function profile may for example be centered at z=0 (i.e. $\Delta$=0). In this case two physical parameters need to be determined ($N_0$ and W) and therefore one independent measurement (for example a PMOR DC measurement) is needed on top of the basic PMOR measurement (see later).

However the doping concentration profile of the sample is not limited to the function profiles mentioned above, but may be any arbitrary function profile $D(X_j, N_{act}, S_{act}, N_{surf}, \ldots)$.

With substantially fully activated doping profile is meant that more than 50%, more preferably more than 60% of the total amount of dopants is activated. Dopant activation may be defined as the percentage of the active dose to the as-implanted dose (as determined for example by Hall measurements).

Determining substrate parameters from a photomodulated reflectance measurement on the reference comprises performing a photomodulated reflectance (PMOR) offset curve measurement on the reference there from determining the surface excess carrier concentration $\Delta N_{sub}$ and excess temperature $\Delta T_{surf}$ and performing a DC reflectance measurement there from determining the DC reflectance $R_0$.

Determining sample parameters from a photomodulated reflectance measurement on the sample using the substrate parameters comprises performing a photomodulated reflectance (PMOR) offset curve measurement on the sample, and performing at least a DC reflectance measurement on the sample.

From at least these two independent measurements, i.e. the photomodulated reflectance (PMOR) offset curve measurement on the sample and the at least a DC reflectance measurement on the sample, determining at least two of the physical parameters that characterize the dopant profile.

For example for a Gaussian profile centered at z=0 (i.e. $\Delta$=0) the two physical parameters which need to be determined are $N_0$ and W.

In general the physical parameters may for example be $X_j$ and $N_{act}$, or for the specific case of a Gaussian profile with $N_0$ and W. Determining at least two of the physical parameters is done based on $\Delta N_{sub}$ and $\Delta T_{surf}$ from the reference PMOR measurement. Additionally at least another sample parameter may be determined before the step of extracting the set of physical parameters from the reference parameters and substrate parameters. For example a sheet resistance ($R_s$) measurement may be performed after the PMOR offset curve measurement and the DC measurement on the sample, there from determining in general one additional physical parameter, for example, $S_{act}$ (or for example $\Delta$ in the case of a generalized Gaussian).

Alternatively a PMOR power curve may be measured there from determining in general one additional physical parameter (which is needed for a reconstruction of the doping profile).

Depending on the complexity of the doping profile, 2 or more physical parameters need to be determined.

Based on the combination of the PMOR offset curve measurements and the DC reflectance measurements on the sample, the set of physical parameters may be extracted from the reference parameters and substrate parameters.

The step of performing the sample measurement may be done prior to the step of performing the reference measurement or vice versa.

According to certain inventive aspects, a reconstruction of the dopant profile is performed based on the combination of PMOR offset curve measurements, DC reflectance measurements and—depending on the number of physical parameters that have to be determined—a number of additional physical measurements such as for example sheet resistance measurements, PMOR power curve measurements, SIMS measurements, electrical AFM measurements (e.g. SSRM), . . . .

Additionally a calibration or fitting step is necessary in order to fit the different physical parameters. The reconstruction step may be performed prior to the calibration step or vice versa.

According to at least some inventive aspects, a new fast, non-destructive and highly local (~1 µm measurement spot) carrier-profiling technique is based on the combined measurement of the PMOR offset curves and of the DC reflectance of a probe laser. The technique has been tested on a variety of B-implanted layers with and without GE PAI. The extracted carrier profiles follow the expected qualitative trends when it comes to annealing temperature and PAI conditions. The profiles also prove to be in good agreement with other profiling techniques such as SIMS or SSRM, with an average accuracy of about 3 nm.

One embodiment also relates to a system for optically determining a substantially fully activated doping profile, the substantially fully activated doping profile being characterized by a set of physical parameters, the system comprising:

a PMOR measurement system comprising a pump laser and a probe laser for obtaining photomodulated reflectance (PMOR) offset curve measurement data and for obtaining DC reflectance measurement data of the probe laser and a processing system for receiving photomodulated reflectance (PMOR) offset curve measurement data and for obtaining DC reflectance measurement data of the probe laser for a sample and a reference and for determining, based on the measurement data values for the set of physical parameters of the doping profile.

One inventive aspect also relates to a computer program product for determining a substantially fully activated doping profile, the substantially fully activated doping profile being characterized by a set of physical parameters, wherein the computer program product is adapted for receiving photomodulated reflectance (PMOR) offset curve measurement data and for receiving DC reflectance measurement data of the probe laser for a sample and a reference and for determining, based on the measurement data values for the set of physical parameters of the doping profile.

One inventive aspect also relates to a machine readable data carrier storing the computer program product as described above or to the transmission of such a computer program product over a network.

Certain aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

The behavior of the phase and wavelength of the plasma wave are recognized in (d) for the four highest annealing temperatures, which ensures that the technique can safely be used on these samples.

Figure 9:
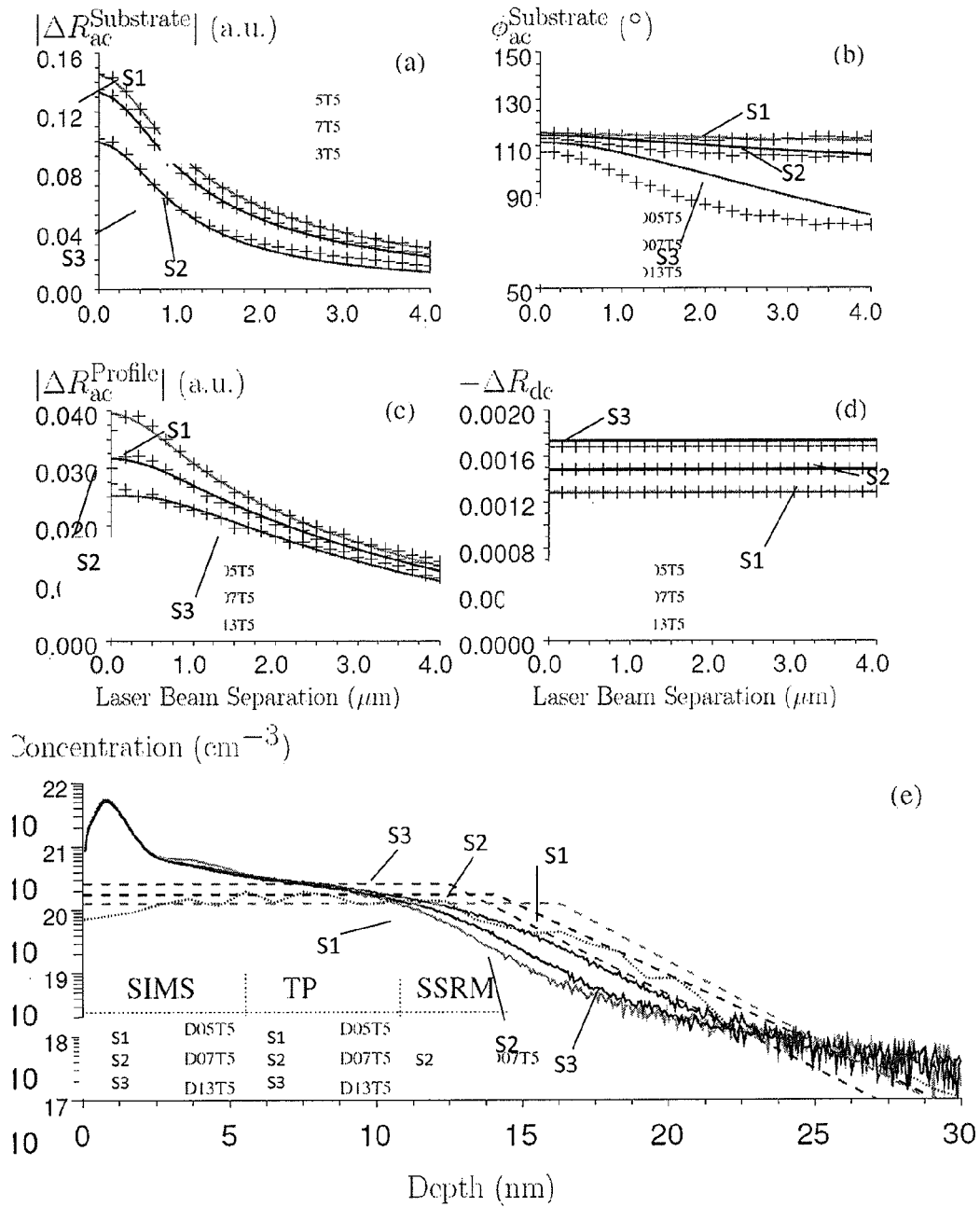

FIG. 9 illustrates fitting curves of experimental data indicating features of one embodiment of the present disclosure. The experimental values for $|\Delta R_{AC}^{substrate}(r)|$ (a), $\phi_{AC}^{substrate}(r)$ (b), $|\Delta R_{AC}^{profile}(r)|$ (c) and $\Delta R_{dc} = R_{dc}^{profile}(r) - R_{dc}^{substrate}(r)$ (d) measured on three samples is shown. FIG. 9 (e) illustrates a comparison of the TP profiles (interrupted lines) with the SIMS profiles (full lines) measured on the samples. The SSRM profile of one of the samples is also shown. The active SIMS doping concentrations are respectively $1.71\times10^{20}$ cm$^{-3}$, $1.80\times10^{20}$ cm$^{-3}$ and $1.80\times10^{20}$ cm$^{-3}$.

Figure 10:
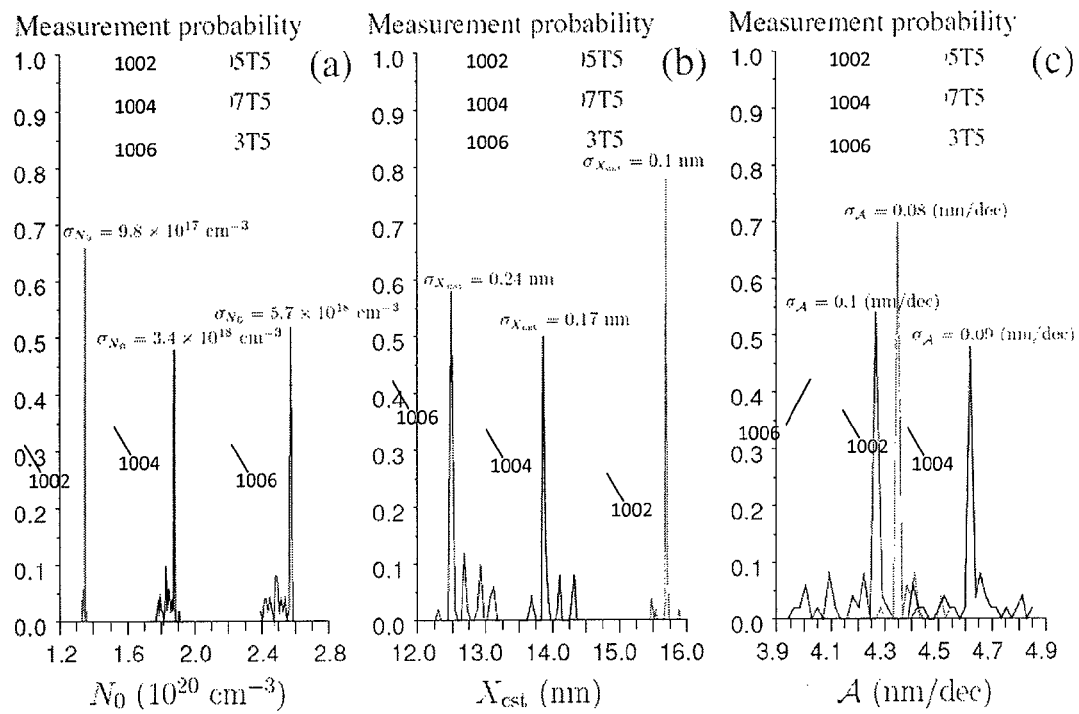

FIG. 10 illustrates measurement probability distributions as obtained from Monte-Carlo simulations of the three profile parameters used in one embodiment of the present disclosure, i.e. (a) the peak active doping concentration $N_0$, (b) the depth $X_{cst}$ at which the profile starts to decay and (c) the abruptness A. The narrow peaks show that the developed technique determines all three fitting parameters with good precision.

Figure 11:
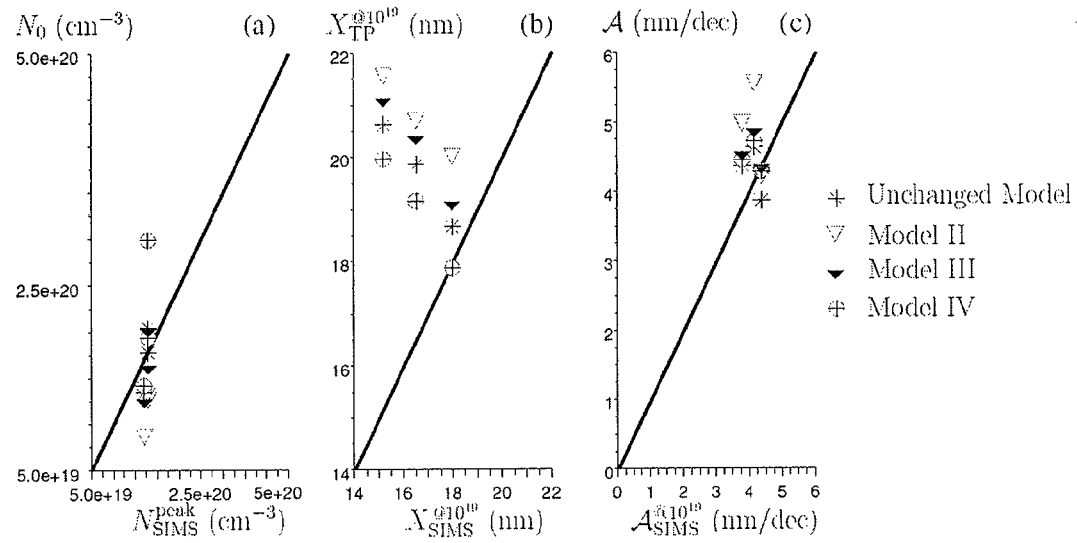

FIG. 11 illustrates the TP versus SIMS profile characteristics and their sensitivity to modeling errors. FIG. 11(a) illustrates a comparison of the peak active doping concentration $N_0$ with the SIMS peak doping concentration $N_{SIMS}^{peak}$ obtained from sheet resistance measurements. FIG. 11(b) illustrates a comparison of the depths $X_{TP}^{at\ 10^{19}}$ and $X_{SIMS}^{at\ 10^{19}}$ at which respectively the TP and SIMS profiles reach a $10^{19}$ cm$^{-3}$ concentration. FIG. 11(c) illustrates a comparison of the TP and SIMS profile abruptnesses A and $A_{SIMS}^{at\ 10^{19}}$ at a $10^{19}$ cm$^{-3}$ concentration. Model II assumes a 30% greater electrorefractive effect, model III assumes a doubled modulated irradiance of the pump laser and Model IV assumes $\Delta N_{sub0} = 2|\Delta N_{sub1}|$.

Figure 12:
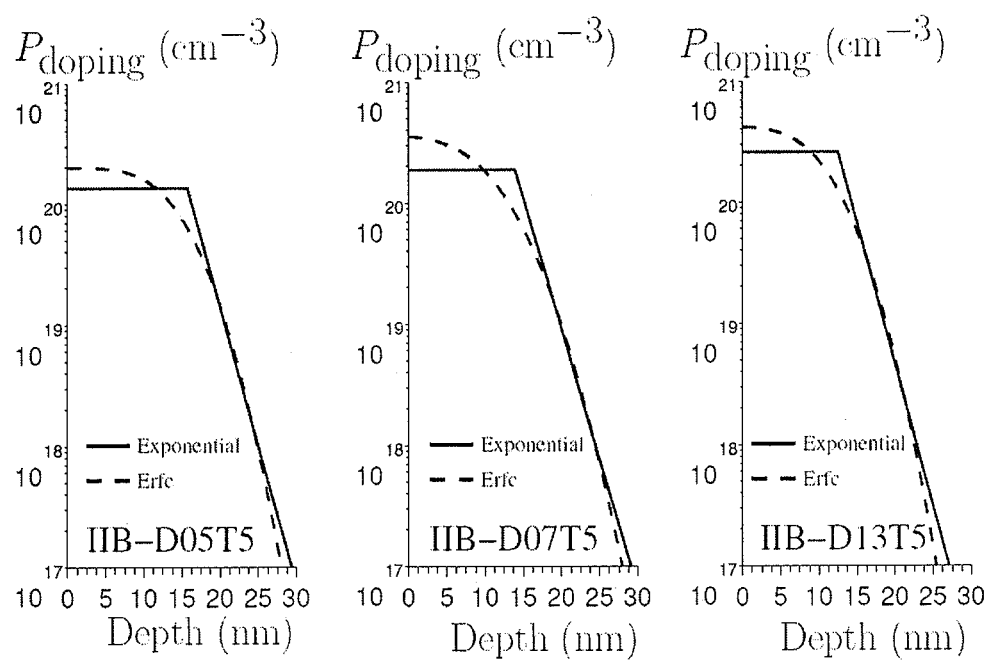

FIG. 12 illustrates a comparison of the TP profiles as obtained from the fitting of the experimental data measured on three samples assuming a profile decaying exponentially (full lines) or a profile following a complementary error function (interrupted lines). While the depth and abruptness are unique, the peak active doping concentration depends upon the profile shape.

Figure 13:
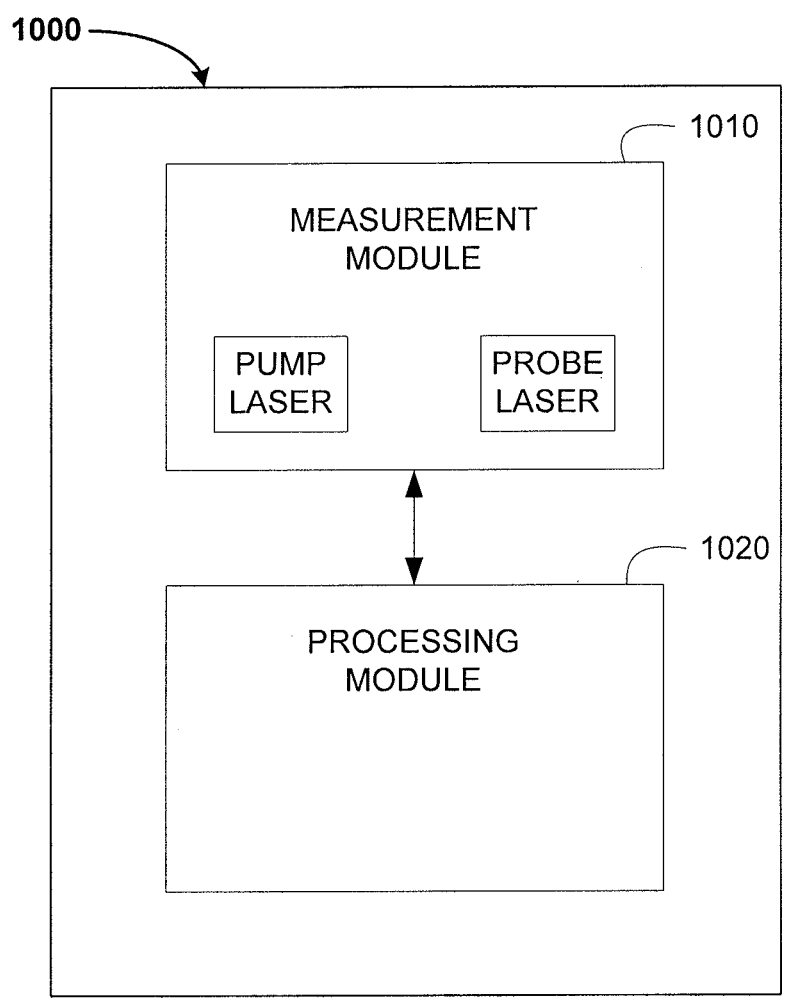

FIG. 13 shows a block diagram illustrating one embodiment of a system for optically determining a substantially fully activated doping profile.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF CERTAIN ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

One embodiment relates to a method for optically determining a substantially fully activated doping profile. The substantially fully activated doping profile is characterized by a set of physical parameters, e.g. by a predetermined profile characterized by a set of physical parameters. Such predetermined profile may be any type of profile, such as for example a Gaussian profile, a Lorentzian profile, a box or box-like profile, embodiments of the present disclosure not being limited thereto. The method comprises obtaining a sample comprising a fully activated doping profile and a reference, whereby the reference may be part of the same sample. The method also comprises obtaining photomodulated reflectance (PMOR) offset curve measurement data and DC reflectance measurement data for the sample comprising the fully activated doping profile and for the reference. The measurement data is advantageously obtained using the same measurement setup, e.g. using a PMOR recording system. For example, the DC reflectance measurement data may be DC reflectance measurement data for DC reflectance of the probe laser used in the PMOR recording system. It is an advantageous that, for obtaining a substantially fully activated dopant profile can be obtained using a relatively simple setup, without the need for measurement equipment different from the PMOR setup. The measurement data may be advantageously obtained simultaneously. The method also comprises determining values for the set of physical parameters of the doping profile based on both the photomodulated reflectance offset curve measurements and the DC reflectance measurements.

Figure 1:
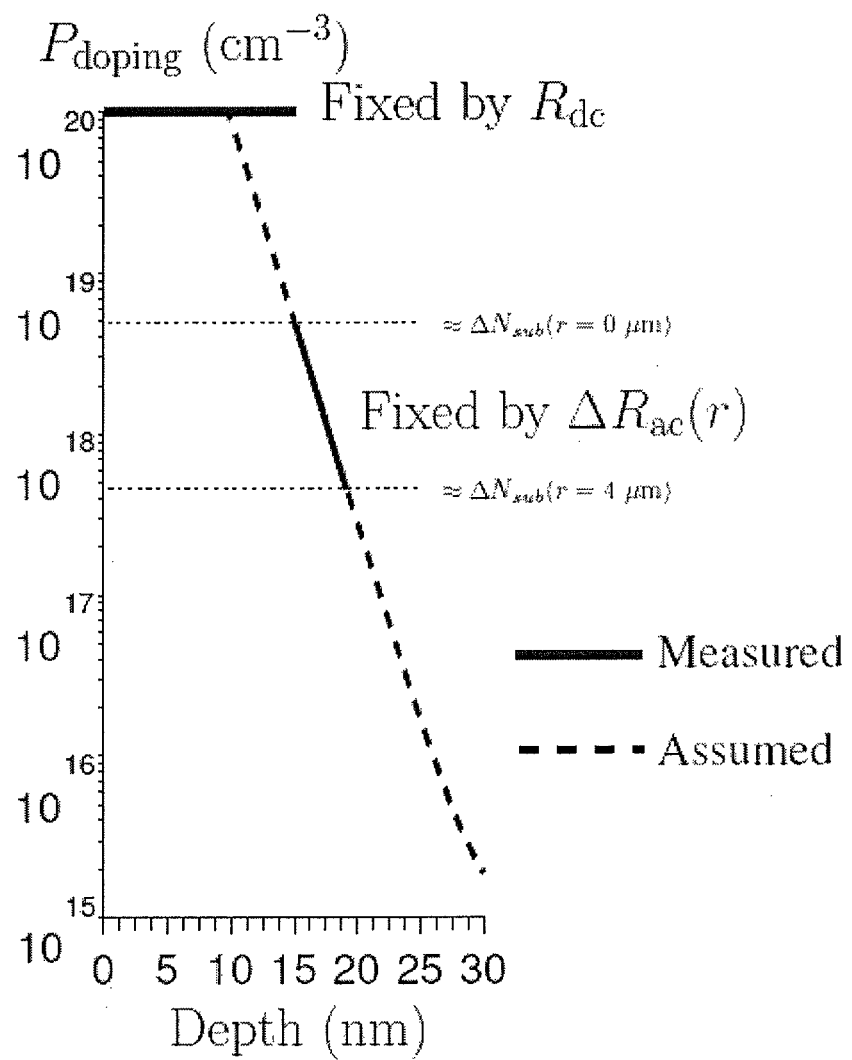
FIG. 1 illustrates the determination of a profile model to an active dopant profile using $R_{dc}$ and $\Delta R_{AC}$ measurements, according to an embodiment of the present disclosure.

Certain embodiments of the present disclosure advantageously make use of DC reflectivity which is linear sensitive to active doping concentration, for obtaining information regarding the doping concentration, and of AC reflectivity obtained through PMOR which is sensitive for lower doping concentrations for determining depth and optionally also abruptness of the active doping profiles. The latter is illustrated in FIG. 1, indicating a profile for the active doping profile, whereby the DC reflectivity measurement data especially contributes for determination of the active doping concentration and wherein the PMOR measurement data especially contributes to the depth and abruptness of the active doping profile. Advantageously, the active doping profile may be described using a predetermined profile characterized with parameters determined using the PMOR and the DC reflectivity measurement data. Such a predetermined profile can also provide further information for such regions where no measurement data were recorded.

Figure 2:
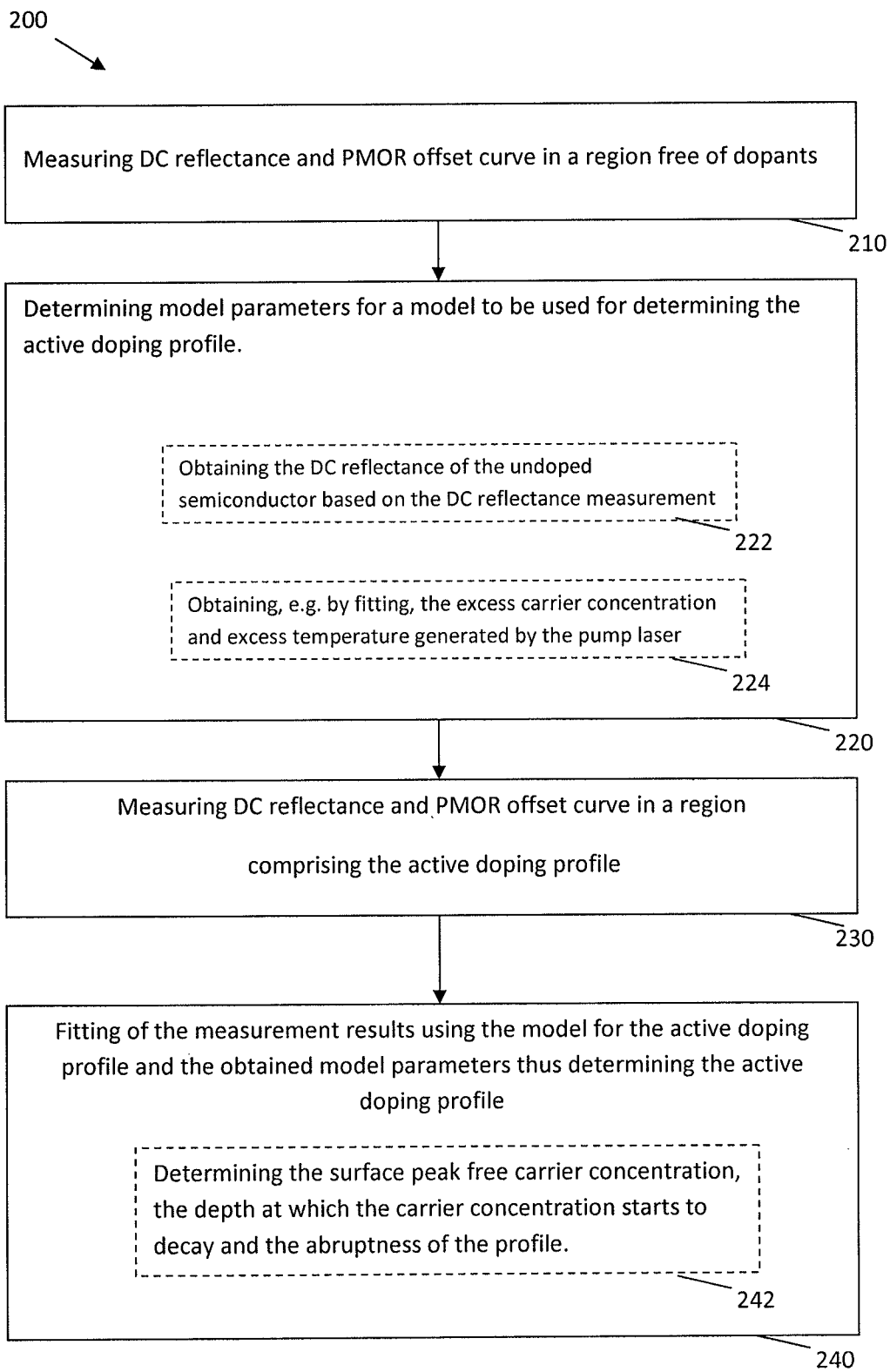
FIG. 2 illustrates an exemplary method for determining an active dopant profile according to a particular embodiment of the present disclosure.

An exemplary technique for determining a carrier profile according to an embodiment of the present disclosure is shown by way of example in FIG. 2, embodiments of the present disclosure not being limited thereto. The exemplary method 200 comprises in a first step measuring 210 a DC reflectance and PMOR offset curves in a region free of dopants. Such measurements allow determining 220 model parameters for the model that will be used for determining the active doping profile to be determined. Determining model parameters 220 may for example in one particular embodiment be determining 222 the DC reflectance of the undoped semiconductor based on the DC reflectance measurement and obtaining 224 the excess carrier concentration and excess temperature generated by the pump laser, although embodiments of the present disclosure are not limited thereto and, depending on the model used, also other model parameters may be derived from the measurements in a region free of dopants. In a subsequent step, the DC reflectance and PMOR offset curves are measured 230 in the region comprising the active doping profile. Based on the measurements obtained in step 230 and on the model parameters determined in step 220, the measurement results are fitted to the model selected for the active doping profile and the active doping profile is thus determined. This is illustrated in step 240. In a particular embodiment, determining the active doping profile may comprise or may be determining the parameters further defining the model for the active doping profile. Such parameters in one example may be the surface peak free carrier concentration, the depth at which the carrier concentration starts to decay and the abruptness of the profile.

By way of illustration, embodiments of the present disclosure not being limited thereto, features and advantages of embodiments of the present disclosure will further be illustrated using exemplary studies that have been performed.

In a first example, a study on a variety of B-implanted layers with different laser-annealing temperatures and various preamorphization (PAI) conditions is presented. The extracted profiles are compared with other characterization techniques. In the study, the data were measured with the ThermaProbe TP630XP tool (TP), a special implementation of PMOR with a pump laser power modulated at high frequency (1 MHz), fixed pump and probe laser wavelengths (resp. 790 nm and 670 nm), fixed pump and probe laser powers (resp. 13.5 mW and 2.5 mW) both focused onto an 0.5 µm beam radius.

By way of illustration, the effect of the free carrier profile on the DC reflectance and on the PMOR offset curves is discussed first theoretically, as techniques according to one embodiment of the present disclosure combine PMOR offset curves with the DC reflectance of a probe laser in order to reconstruct carrier profiles. It is to be noticed that embodiments of the present disclosure should not be considered limited by or to such theoretical considerations or the mathematical formalism used.

The PMOR signal is a measure of the change $\Delta R$ in reflectance of the probe laser due to the injection by the pump laser of excess carriers and heat (resulting in surface excess temperature $\Delta T_{surface}$) The case of a sample with an arbitrary carrier profile $N_{act}(z)$ (z representing depth), can be described as follows:

The in-depth and lateral excess carrier distribution $\Delta N(z,x)$ is given by $$\Delta N(z,x) = \Delta N[N_{act}(z), \Delta N_{sub}(x)]$$

and depends upon the (equilibrium) free carrier profile $N_{act}(z)$ as well as the substrate injection $\Delta N_{sub}(x)$, where x represents the lateral distance between the probe and pump lasers. Due to the fast in-depth variations of this excess carrier distribution, the PMOR signal of a probe laser with wavelength $\lambda_{probe}$ has to be written as $$\frac{\Delta R}{R_0}(x) = \frac{4}{(n_0^2 - 1)} \left\{ -\beta\left(\frac{1}{m_e} + \frac{1}{m_h}\right) \left[ \begin{array}{l} \Delta N[N_{act}(z=0), \Delta N_{sub}(x)] + \\ \int_{0+}^{+\infty} \frac{\partial \Delta N[N_{act}(z), \Delta N_{sub}(x)]}{\partial z} \cos\left(\frac{4\pi n_0 z}{\lambda_{probe}}\right) dz \end{array} \right] + \delta \Delta T_{surf}(x) \right\}$$

where $m_e$ (respectively $m_h$) is the effective mass of electrons (respectively holes) in silicon. $R_0$ is the DC reflectance of undoped Si, $n_0$ is the refractive index of undoped Si, $\beta$ is the Drude coefficient, $\delta = \partial n/\partial T$ is the temperature coefficient of the refractive index in Si, all four taken at wavelength $\lambda_{probe}$. The above equation shows that the PMOR signal can be understood as the coherent sum (interference) of the reflections occurring at all depths of the excess carrier profile (including a thermal component at the surface expressed by the last component between the brackets). The link between the excess carrier distribution $\Delta N[N_{act}(z), \Delta N_{sub}(x)]$ and the (equilibrium) free carrier profile $N_{act}(z)$ is known by the person skilled in the art. For determining PMOR offset curves, the PMOR signal as given by the equation above is measured as a function of the distance x between the probe and the pump beams (with a maximum distance of 4 µm). Measured simultaneously with the PMOR signal, the DC reflectance R of the probe laser is also influenced by the (equilibrium) free carrier profile. The variation in DC reflectance $\Delta R_{DC}$ at wavelength $\lambda_{probe}$ due to a hole profile $N_{act}(z)$ is given by $$\Delta R_{DC} = R - R_0 = -\frac{4\beta(n_0 - 1)}{m_h(n_0 + 1)^3} \left[ N_{act}(z=0) + \int_{0+}^{+\infty} \frac{\partial N_{act}(z)}{\partial z} \cos\left(\frac{4\pi n_0 z}{\lambda_{probe}}\right) dz \right].$$

According to this equation, $\Delta R_{DC}$ is easily understood as the coherent sum of the reflections occurring at all depths of the (equilibrium) free carrier profile. In other words, the DC reflectance is a direct image of $N_{act}(z)$, whereas the PMOR signal is an indirect image of $N_{act}(z)$ [via $\Delta N$]. When it comes to the sensitivity to carrier profiles, the combination of the PMOR offset curves with the DC reflectance is very promising. PMOR offset curves have been shown to be essentially sensitive to the depth of the profile. Second, the change in DC reflectance is directly proportional to the peak carrier concentration, as can be seen from the above formula. In other words, the combination of both measured parameters gives access to the depth of the profile (mostly via the PMOR offset curve) and to the carrier concentration of the profile (mostly via the DC reflectance).

In the present example, for each profile, the measurement and fitting procedure is divided into two phases. Both phases involve a measurement and the fitting of the obtained data. The fitting algorithms in the exemplary study discussed is based on a Levenberg-Marquardt optimization algorithm, embodiments of the present disclosure not being limited thereto.

In a first phase I, also referred to as the calibration phase, the three parameters appearing in the equations above which are not linked to the free carrier profile, i.e. $\Delta N_{sub}(x)$, $\Delta T_{surf}(x)$, $R_0$ were fixed. These three parameters were then used in Phase II. For this purpose, the DC reflectance and the PMOR offset curve on a region free of dopants was measured. First the measured DC reflectance determined the reference $R_0$. Second, the PMOR offset curve was fitted with, as sole fitting parameters, the carrier recombination lifetime and ambipolar diffusivity. At each step of the optimization loop, the three-dimensional linear ambipolar diffusion equation and heat equation were solved. This determined $\Delta N_{sub}(x)$ and $\Delta T_{surf}(x)$, i.e. the excess carrier concentration and excess temperature generated by the pump laser in the Si substrate. Importantly $\Delta N_{sub}(x)$ and $\Delta T_{surf}(x)$ are influenced by any possible damage of the substrate, as is the case in preamorphized layers. For each sample, the calibration phase therefore advantageously was measured on a site free of any dopant, but having undergone the same preamorphization implant PAI (and anneal) as the considered doped sample. For this reason, during the processing of each ultra-shallow profile, a lithographic step was performed in order to keep a region free of dopants. Except for this additional step, the dopant free regions followed the same process as the doped regions, making them ideal candidates for the calibration of $\Delta N_{sub}(x)$ and $\Delta T_{surf}(x)$. It thereby was assumed that the B implant induces negligible extra damage to the sample.

In a second phase II, also referred to as a reconstruction phase, the PMOR offset curves and the DC reflectance on the considered active doping profile were measured. The data were then fitted with a carefully parameterized profile. For uniqueness reasons, restriction was performed to two-parameter or three-parameter profiles (box, Gaussian, Lorentzian, . . . ) whereby below the example of box profiles with an exponential tail (three parameters) is discussed. In other words, the fitting profiles used in the present exemplary study can be written $$N_{act}(z) = \begin{cases} N_0 & \text{for } z \leq X \\ N_0 \times 10^{-z/\alpha} & \text{for } z > X \end{cases}$$

where $N_0$ is the surface (peak) free carrier concentration, X is the depth at which the carrier concentration starts to decay and $\alpha$ is the abruptness of the profile. The fitting algorithm optimizes $N_0$, X and $\alpha$ based on the above equations and using the values of or $R_0$, $\Delta N_{sub}(x)$, $\Delta T_{surf}(x)$ determined in the calibration phase.

The above technique was used on a series of 0.5 keV B-implanted samples with two different doses ($5 \times 10^{14}$ at·cm$^{-2}$ and $10^{15}$ at·cm$^{-2}$). All layers were implanted in lowly doped n-type (monitor) wafers. A Ge preamorphization implant (PAI) was also applied. The PAI conditions varied in energy (from 5 keV to 20 keV) as well as dose ($10^{14}$ at·cm$^{-2}$ and $5.10^{14}$ at·cm$^{-2}$). For each B dose, a reference wafer without PAI was also added. All samples were laser annealed by 3-scan anneals (150 mm·s$^{-1}$) using five different temperatures ranging from 1150° C. to 1300° C.

It has to be kept in mind that the PMOR signal is sensitive to the free carrier profile only via the plasma component of the above formula. The plasma component therefore advantageously should dominate the thermal component. The latter is obtained by using high activation in the layer and low (end-of-range) defect concentrations. Typically, the higher the preamorphization implant (PAI) dose or energy, the higher the annealing temperature that advantageously is used, as this improves the usability of the technique.

Figure 3:
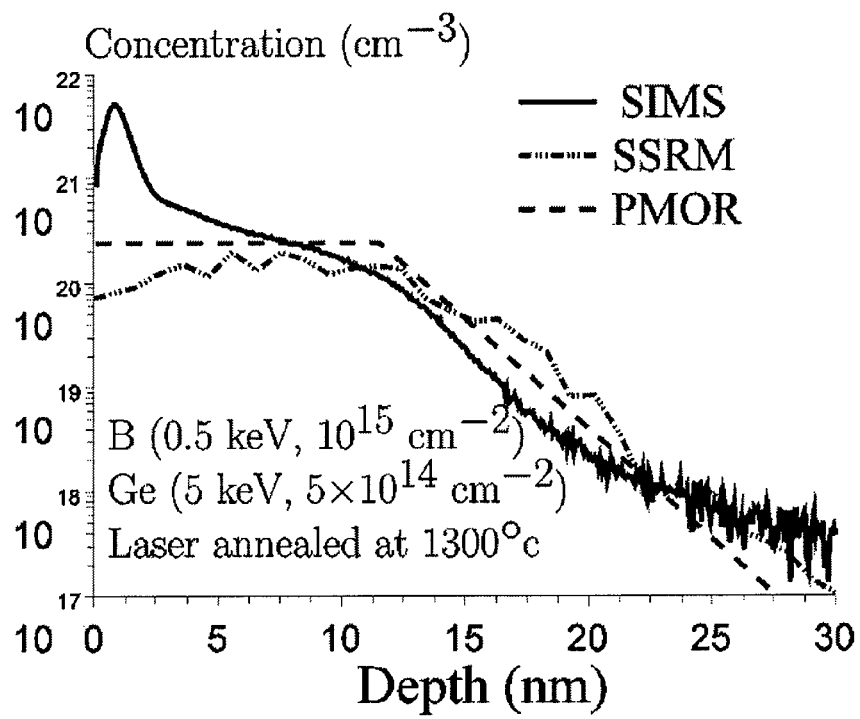
FIG. 3 illustrates a comparison between the SIMS profile (total doping), SSRM profile (free carriers) and PMOR (free carriers) of a sample implanted with B (0.5 keV, $10^{15}$ cm$^{-2}$) after Ge preamorphization (5 keV, $5\times10^{14}$ cm$^{-2}$) and annealed at 1300° C., illustrating advantages of one embodiment of the present disclosure.

Except for the cases of insufficient activation, the obtained profiles were in agreement with the expected trend with annealing temperature, i.e. they become more actively doped and slightly deeper as the annealing temperature increases. Similarly, the impact of the presence of a PAI on the extracted profiles also followed the expectations. The annealing temperature indeed had less impact on the peak concentration and the depth of the profiles when applying a PAI, as expected from sheet resistance measurements. To assess the quality of the obtained carrier profiles, these were compared with other characterization techniques. The obtained profiles were compared with Secondary Ion Mass Spectrometry (SIMS)p and Scanning Spreading Resistance Microscopy (SSRM). FIG. 3 shows a comparison between the measured SIMS, SSRM and PMOR profiles on a sample implanted with high B dose ($10^{15}$ cm$^{-2}$) after Ge preamorphization (5 keV, $5 \times 10^{-14}$ cm$^{-2}$) and annealed at 1300° C. An excellent agreement was observed between all three techniques.

As neither SIMS nor SSRM are direct measurements of the carrier profile, in contrast to PMOR, a more quantitative comparison of the profiles was difficult. SIMS measures the total (i.e. electrically active and inactive) doping profile and SSRM measures the resistivity profile. It has been shown that it is possible to extract the carrier profile from a SIMS measurement if the sheet resistance and carrier mobility are available. Similarly, carrier profiles can be deduced from SSRM measurements only if the carrier mobility is known. For instance, the SSRM profile in FIG. 3 assumes a hole mobility of 100 cm$^2$·V$^{-1}$·s$^{-1}$ in the doped layer. In other words, whether using SIMS or SSRM, mobility is always needed if one wants to extract carrier profiles.

When focusing on SIMS measurements, one should measure sheet resistance and mobility for correct comparison. Sheet resistance has been measured using a Four-Point Probe (FPP). As for mobility, since measured values are not available yet, two different mobility models are used, respectively setting upper and lower limits to the mobility range (hence defining respectively lower and upper limits of the active doping concentration range). Both mobility values are obtained using Klaassen's model. To determine an upper limit of the mobility range, a first model considered only the carrier scattering upon active dopants (no scattering on inactive dopants). This is also referred to as model I. It is, however, well-known that this assumption tends to overestimate the mobility in a ultra-shallow junction USJ. As a consequence, the obtained carrier concentration will be underestimated. A second model assumed that all the B atoms measured in the SIMS profile are scattering centers. This is also referred to as model II. This proves to underestimate the mobility strongly and therefore to overestimate considerably the active doping (above solid solubility in most cases). The depth and abruptness of the profiles stay obviously the same using one model or the other.

Figure 4:
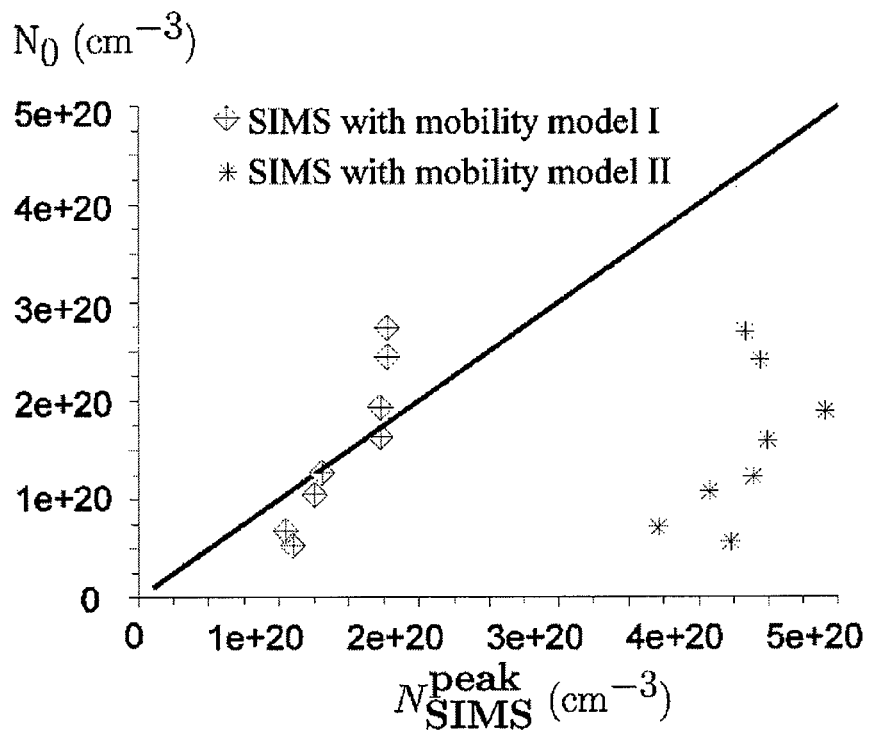
FIG. 4 illustrates a comparison between the peak concentration of the PMOR profile and the peak concentration of the active SIMS profile of 8 selected layers. Diamond symbols represent the peak SIMS active doping concentration using mobility model I and the stars using mobility model II. The full line represents the 1-1 correlation.
Figure 5:
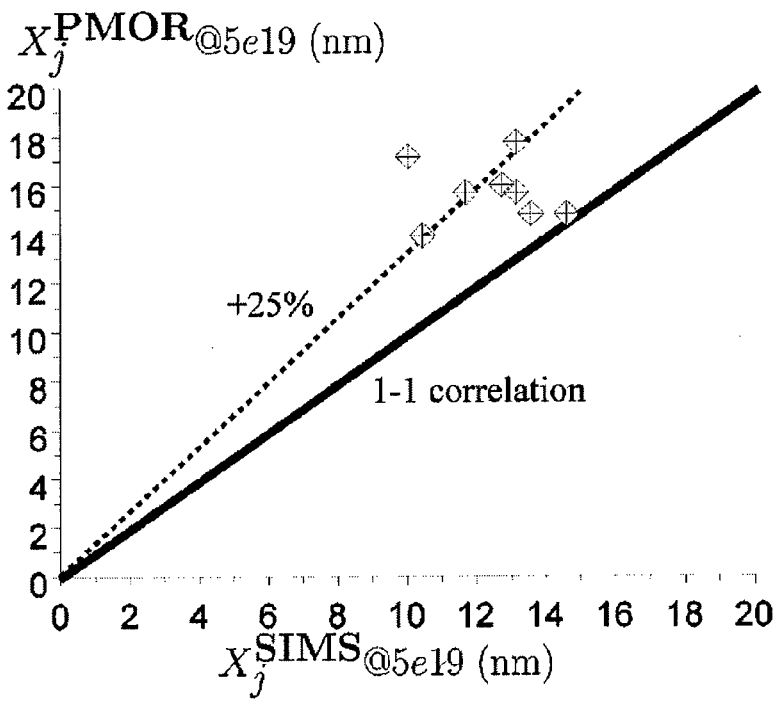
FIG. 5 illustrates a comparison between the depths of the PMOR and SIMS profiles at a concentration of 5e19 cm$^{-3}$ of 8 selected layers. The full line represents the 1-1 correlation and the dotted line represents the case of a PMOR profile 25% deeper than the SIMS profile.
Figure 6:
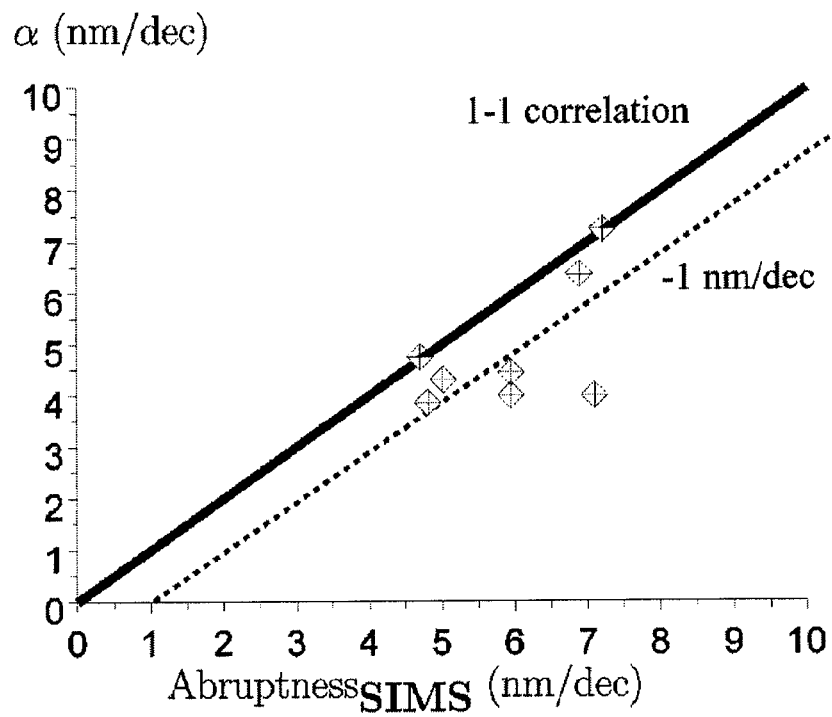
FIG. 6 illustrates a comparison between the abruptness of the PMOR and SIMS profiles of 8 selected layers. The full line represents the 1-1 correlation and the dotted line represents the case of a PMOR profile 1 nm/dec steeper than the SIMS profile.

The comparison between SIMS and PMOR profiles is summarized in FIG. 4 and FIG. 5 and FIG. 6. In particular, FIG. 4 shows the correlation between the peak concentration $N_0$ of the extracted PMOR profile and the peak concentration of the active SIMS profiles. As explained above, two mobility models are used for determining mobility for use in the SIMS measurements giving two peak active SIMS doping concentration for comparison. It can be checked that $N_0$ is in good agreement with SIMS using the first mobility model I (diamonds). It can also be observed that, as expected, $N_0$ is always much lower than the SIMS values obtained with the second mobility model II (stars). FIG. 5 compares the depth of the PMOR and SIMS profiles at a concentration of 5e19 cm$^{-3}$. It can be observed that PMOR almost systematically overestimates the depth of the profile, as given by SIMS. This could actually also be observed in FIG. 3 and can be explained by the probable overestimation of $\Delta N_{sub}(x)$ (due to calibration). Finally, FIG. 6 compares the abruptness of the PMOR and SIMS profiles. The agreement here also was very good though PMOR profiles are systematically slightly steeper (typically 1 nm/dec).

In a second example, a second study is provided illustrating features and advantages of one embodiment of the present disclosure. Without wishing to be bound by theory, features and advantages may be further explained by the following theoretical considerations, embodiments of the present disclosure not limited thereby, nor by the mathematical formalism used. The study indicates that the combined use of $\Delta R_{AC}$ and $R_{dc}$ allow for the simultaneous measurement of the depth, abruptness and active doping concentration of a profile, i.e. for substantially determining the profile.

On a profile of arbitrary shape, $\Delta R_{AC}$ can be written as $$\Delta R_{ac}^{Profile}(r) = \frac{4R_0}{n_0^2 - 1}\Gamma_0 \exp(-i\theta_0) \times \left\{-\beta\left(\frac{1}{m_e} + \frac{1}{m_h}\right)\Delta N_{fl}(r, z=0) + \delta\Delta T_1(r) - \beta\left(\frac{1}{m_e} + \frac{1}{m_h}\right)\int_{0+}^{+\infty}\frac{\partial \Delta N_{fl}(r,z)}{\partial z}\cos(4\pi n_0 z/\lambda_{probe})dz\right\}$$

Figure 7:
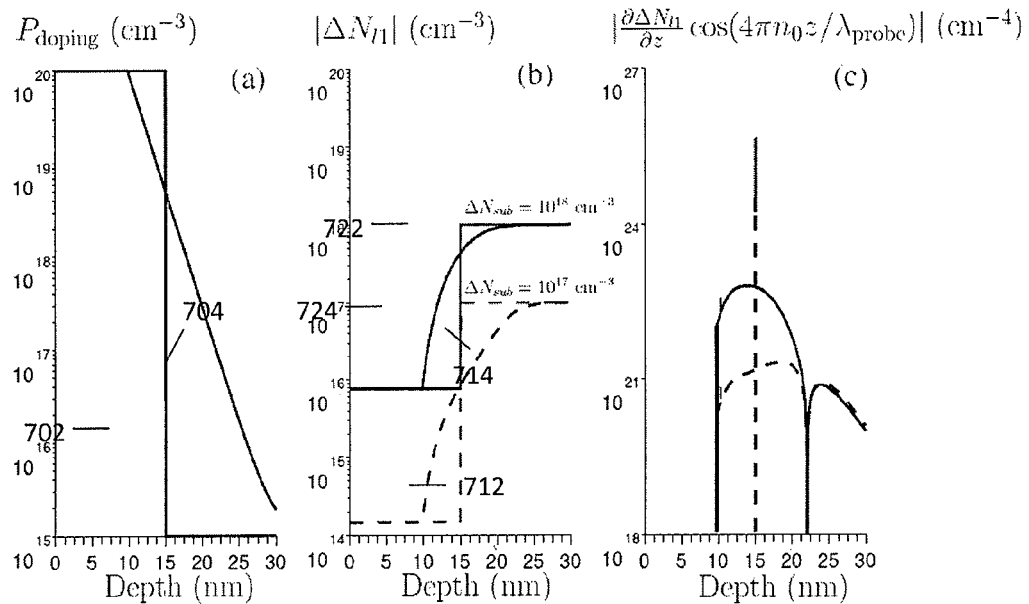
FIG. 7 illustrates principles as can be used in one embodiment of the present disclosure. A comparison of a profile of infinite slope, i.e. a box like profile, with a profile of a finite slope is shown (a), subsequent excess carrier profiles when the substrate carrier concentration is of $10^{17}$ cm$^{-3}$ (interrupted lines) and $10^{18}$ cm$^{-3}$ (full lines) for both the profile with finite slope and the profile with infinite slope are shown (b) and the behavior of the integrand in the equation for $\Delta R_{AC}$ for arbitrary profiles is shown (c).

$\Delta R_{AC}$ can be understood as the coherent sum of two reflections. The first reflection occurs at the surface and is due to both the surface excess carriers $\Delta N_{fl}(z=0)$ and the excess temperature $\Delta T_1$. The second reflection is occurring at each depth of the excess carrier profile. FIG. 7 illustrates the analogy. More particularly, it shows two active doping profiles with different slopes (FIG. 7a illustrating a profile of infinite slope 702 and a profile of a finite slope 704)) and the subsequent excess carrier profiles for two different excess carrier concentrations in the substrate for $10^{17}$ cm$^{-3}$ and $10^{18}$ cm$^{-3}$ (FIG. 7b indicating the subsequent excess carrier profiles when the substrate carrier concentration is of $10^{17}$ cm$^{-3}$ for the infinite slope 712 and the finite slope 714 and when the substrate carrier concentration is of $10^{18}$ cm$^{-3}$ for the infinite slope 722 and the finite slope 724). The behavior of the integrand of the above equation is shown in FIG. 7c for all four situations. On the one hand, in the case of a box-like profile, the integrand of the above equation reduces to a peak at the junction, i.e. the interface reflection is composed of one single large reflection. Furthermore, the position of this peak is independent from the substrate injection. On the other hand, when the slope of the profile is finite, the multiple reflections at the interface broaden the peak. The position of the maximum of this peak, i.e. the maximum interface reflection, can be understood as the depth to which $\Delta R_{ac}$ is sensitive. As can be seen in FIG. 7c, in the case of a profile with a finite slope, the maximum interface reflection moves according to the substrate injection. Mathematically, this can be understood as follows: Neglecting the cosine envelope of the integrand, the position $z_{max}$ of the maximum interface reflection can be defined as the position at which the excess carrier profile is the steepest, i.e. an approximate value of $z_{max}$ can be found by solving the following implicit equation $$\left.\frac{\partial^2 \Delta N_{fl}(z)}{\partial z^2}\right|_{z=z\,max} = 0$$

$$\Leftrightarrow \frac{\frac{\partial^2 [P_{doping}(z\,max)/\Delta N_{sub}]}{\partial z^2}}{\left\{\frac{\partial [P_{doping}(z\,max)/\Delta N_{sub}]}{\partial z}\right\}^2}$$

$$= \frac{1}{\sqrt{4 + P_{doping}^2(z_{max})/\Delta N_{sub}^2}}$$

$$\left(1 + \frac{1}{\sqrt{1 + 4\Delta N_{sub}^2/P_{doping}^2(z_{max})}}\right)$$

whereby use is made of an assumption regarding Bolzmann statistics and neglection of BGN. The above equation simply signifies that the depth of the maximum interface reflection depends solely on the function $P_{doping}(z)/\Delta N_{sub}$ and its derivatives. When taking the example of an active doping profile decaying with an exponential tail, the maximum interface reflection occurs at a depth $z_{max}$ and $$\frac{P_{doping}(z=z_{max})}{\Delta N_{sub}} = \sqrt{2(-1+\sqrt{5})} \approx 1.57,$$

i.e. the maximum interface reflection comes from the depth where the doping concentration is $1.57 \times \Delta N_{sub}$. From this result, it is correct to extrapolate that the maximum interface reflection always originates from a depth where the doping is commensurate with the substrate injection, independently from the profile itself. Note that the particular value obtained in the above equation, however, cannot be generalized for all profiles since the profile derivatives are involved.

In conclusion, from the above it can be seen that $\Delta R_{AC}$ is sensitive to the depth at which the active doping profile reaches a concentration of the order of the substrate injection. This has two important implications. First it means that, in the measurements performed, $\Delta R_{AC}$ is only sensitive to the moderately doped region of the profile. Second if the injection level can somehow be changed, the position of the maximum interface peak is shifted accordingly, i.e. part of the profile is scanned. This explains the sensitivity of offset curves to the abruptness of the profiles, as a direct consequence of the lower carrier injection when moving away from the pump beam.

Concerning the DC reflectance $R_{dc}$, contrary to $\Delta R_{AC}$, it is known that it is mostly sensitive to the highly doped region of the profile. It can be understood that $R_{dc}$ fixes the peak doping concentration based on the depth and abruptness determined by $\Delta R_{AC}$ in the moderately doped region of the profile, as is also illustrated and described above with reference to FIG. 1, illustrating features of the principle of the technique of one embodiment of the present disclosure. It is to be noticed that since $\Delta R_{AC}$ is blind to the region of the profile situated above a $10^{19}$ cm$^{-3}$ doping concentration, the peak concentration determined by $R_{dc}$ depends on the assumed shape of the profile in that particular region. The corresponding uniqueness problem is solved by selecting a good profile shape for the active dopant profile. In the present exemplary study, a method as described above with reference to FIG. 2 was used for determining the active dopant concentration. Further features of the exemplary method are described below.

The method comprises measuring DC reflectance and PMOR offset curve in a region free of dopants. In other words, a substrate or reference measurement is run, i.e. a measurement on a sample presenting no doped layer but having undergone the same process flow as the sample under investigation. For instance, in the case of an annealed implanted layer, the substrate measurement is run on a region of the sample which has received no dopant implant but has been preamorphized (if relevant) and annealed exactly like the doped sample under investigation. This measurement yields $\Delta R_{ac}^{Substrate}$ offset curves and $R_{dc}^{substrate}$ reflectance.

The method also comprises determining model parameters for a model to be used for determining the active doping profile. The DC reflectance $R_0$ can be derived from the $R_{dc}^{substrate}$ reflectance. The model for the AC reflectance on homogeneous samples can be fitted to the experimental $\Delta R_{ac}^{Substrate}$ offset curves for determining the excess carrier distribution in the substrate, i.e. $\Delta N_{sub0}(r)$ and $\Delta N_{sub1}(r)$ and the excess temperature $\Delta T_1(r)$. The index sub0 refers to the time independent mode, whereas the index sub1 refers to the time dependent mode.

The method also comprises measuring DC reflectance and PMOR offset curve in a region comprising the active doping profile. In other words, a profile measurement is run on the sample to be characterized. This yields $\Delta R_{ac}^{profile}$ offset curves and $R_{dc}^{profile}$.

The method further comprises fitting of the measurement results using the model for the active doping profile and the obtained model parameters thus determining the active doping profile. The model for AC and DC reflectances on non-homogeneous samples therefore typically is fitted to the experimental $\Delta R_{ac}^{profile}$ offset curves, using the previously determined $\Delta N_{sub0}(r)$, $\Delta N_{sub1}(r)$ and $\Delta T_1(r)$ and to the experimental $\Delta R_{dc} = R_{dc}^{profile} - R_{dc}^{substrate}$.

As the measurements offer not all information, some constraint on the profile shape advantageously are imposed. The profile shape may be determined by two or three parameter fittings. In the case of annealed implanted layers, box-like profiles with an exponential tail were used and seemed to provide appropriate results, i.e.

$$P_{doping}(z) = N_0 \text{ if } z \leq X_{cst}$$

$$= N_0 \times 10^{-(z-X_{cst})/A} \text{ if } z > X_{cst}$$

where $N_0$ is the peak active doping concentration of the profile, $X_{cst}$ is the depth at which the profile starts to decay and A is its abruptness (nanometer/decade). The fitting algorithm determines $N_0$, $X_{cst}$, and A.

Figure 8:
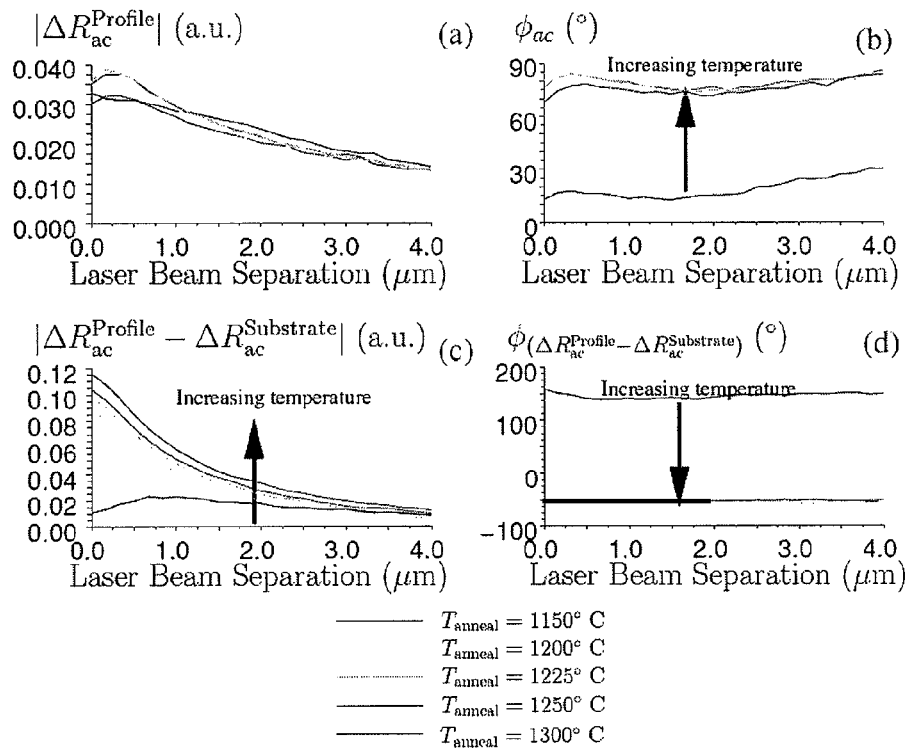
FIG. 8 illustrates offset curves, i.e. curves as function of the laser beam separation, as can be used in one embodiment of the present disclosure, indicating the amplitude of the AC reflectance $\Delta R_{AC}^{profile}$ (a), the phase of the AC reflectance $\Delta R_{AC}^{profile}$ (b), the amplitude of the difference $[\Delta R_{AC}^{profile}(r) - \Delta R_{AC}^{substrate}(r)]$ (c) and the phase of the difference $[\Delta R_{AC}^{profile}(r) - \Delta R_{AC}^{substrate}(r)]$. Measurements are illustrated for five samples implanted on the same substrate with B (0.5 keV, $10^{15}$ cm$^{-2}$) after a Ge preamorphization implant (5 keV, $5\times10^{14}$ cm$^{-2}$) and laser annealed at 1150° C., 1200° C., 1225° C., 1250° C. and 1300° C. The arrows show the trend observed when increasing the annealing temperatures.

The fitting in the present example is based on a Levenberg-Marquardt algorithm (minimization of the least-square error). The technique in the present example relies on the substrate measurement for the determination of the substrate plasma and thermal components. As a consequence, the substrate measurement advantageously is carefully monitored. In the case of an arbitrary profile, a verification procedure can be used to make sure that the substrate measurement meets the requirement, i.e. $\Delta N_{sub0}(r)$, $\Delta N_{sub1}(r)$ and $\Delta T_1(r)$ are the same in the substrate and profile measurements. One method for verifying this may be subtracting the substrate measurement $\Delta R_{ac}^{Substrate}$ from the profile measurement $\Delta R_{ac}^{Profile}$ measured on the unknown doped profile. Since the result of this subtraction should eliminate the thermal component, the phase and wavelength of the plasma wave should be recognized. This is illustrated in FIG. 8. The plasma phase and wavelength can be identified in FIG. 8(d) for all layers except the lowest annealing temperature, underlying the thermally dominated behavior of the latter. The latter also shows that the impact of the boron-implantation-induced damage on the plasma and thermal components is negligible (after anneal).

Using the method as describe above, a number of experimental results were obtained. Taking into account the inaccuracies of the model of the present example, the technique was only used in the current example for highly doped layers (>$10^{20}$ cm$^{-3}$), as for these high concentrations the sensitivity of $\Delta R_{AC}$ to doping vanishes allowing converging of the combined fitting of $\Delta R_{AC}$ and $R_{dc}$. The method as described above has been applied to B-implanted layers laser annealed with a high temperature. In particular, results are provided for three samples having received the same B implant (energy 0.5 keV, dose=$10^{15}$ cm$^{-2}$) and anneal (laser annealed three times at 1300° C.) but different Ge preamorphization implants (PAI), i.e. respectively (5 S1:keV, $10^{14}$ cm$^{-2}$) S2:5 keV, 5×$10^{14}$ cm$^{-2}$) and (S3:20 keV, $10^{14}$ cm$^{-2}$).

The fitted curves are shown in FIGS. 9 (a) and (b) for the substrate measurement and (c) and (d) for the profile measurement. It is clearly observed that the theoretical curves nicely fit the experimental data. The so-called TP profiles obtained from the fitted data are shown in FIG. 9(e) together with the SIMS profiles measured on the three samples. The SSRM profile measured on one of the samples has also been added (assumed mobility is 100 cm$^2$V$^{-1}$s$^{-1}$). The TP profiles have been obtained in less than 30 minutes (20-minute measurement and less than 10 minutes fitting). On average, the quantitative agreement between the TP and active SIMS (and SSRM) profiles is acceptable since the average deviation on the derived depths at a doping of $10^{19}$ cm$^{-3}$ is of 3 nm. The average deviation on the peak active doping concentration is of 5×$10^{18}$ cm$^{-3}$.

The TP profiles in the present example are deeper than the SIMS profiles. TP and SIMS are also in contradiction when it comes to the relative depths of the three profiles.

For completeness, as shown in FIG. 9, only the amplitude of $\Delta R_{ac}^{Profile}$ is fitted. The phase has indeed been ignored in the fitting algorithm of the present example. This is an acceptable approximation for shallow layers where the phase mostly indicates the importance of the thermal component. The determination of the thermal component is taken care by fitting the substrate measurement, where the phase is of extreme importance and therefore taken into account FIG. 9b. It can be checked that the experimental phase and the theoretical phase after fitting of the profile measurement are in acceptable agreement.

In order to assess the precision of the developed technique and determine whether the discrepancies observed in FIG. 9e are due to random errors, the following iterative Monte-Carlo approach was used. First, at each iteration, noisy data were simulated by adding random noise on top of our experimentally measured data. The noise on the measured $\Delta R_{ac}^{Profile}$ and $R_{dc}^{Profile}$ is assumed to follow a normal distribution, the standard deviation of which is given by the signal repeatability, i.e. respectively $\sigma_{\Delta R_{ac}} = 7 \times 10^{-4}$ (a.u.) and $\sigma_{R_{dc}} = 5 \times 10^{-6}$. To take all possible random errors into account, noise is also added on the substrate measurement data i.e. substrate $\Delta R_{ac}^{substrate}$ and $R_{dc}^{substrate}$. Second, the simulated noisy curves are plugged into our fitting procedure described above. The fitting values of the three profile parameters $N_0$, $X_{cst}$ and A are recorded along the iterations.

Limiting to 50 iterations, the measurement probability distributions shown in FIG. 10 is obtained, indicated for the three examples by curves 1002, 1003, 1006. The respective precisions $\sigma_{N_0}$, $\sigma_{X_{cst}}$ and $\sigma_A$ of the three profile parameters $N_0$, $X_{cst}$ and A are defined as the standard deviations of their respective distributions. It can be observed that all three parameters are determined with very high precision. It can also be noted that the peaks of $X_{cst}$ in FIG. 10 (b) are clearly separated. As a conclusion, random errors cannot explain the discrepancy between the TP and SIMS profiles observed in FIG. 9(e).

Since the technique proves to determine the profile characteristics with a high precision, it can be expected that the discrepancies between the TP and SIMS profiles are due to systematic errors and, in particular, to the inadequate accuracy of our model to account for the active doping dependence of the signals.

FIG. 11(a) shows the comparison of peak active doping concentration $N_0$ obtained from our measurement technique with the peak active doping concentration $N_{SIMS}^{at\ 10^{19}}$ obtained from SIMS and sheet resistance measurements (bulk mobility assumed). FIG. 11(b) shows the comparison of the depths $X_{TP}^{at\ 10^{19}}$ and $X_{SIMS}^{at\ 10^{19}}$ at which respectively the TP and SIMS profiles reach a concentration of $10^{19}$ cm$^{-3}$. Finally, FIG. 11(c) compares the abruptnesses A and $A_{SIMS}^{at\ 10^{19}}$ of respectively the TP and SIMS profiles (value taken around a $10^{19}$ cm$^{-3}$ concentration). Different models are used to indicate the effect of variation of parameters.

Model II shows an impact of a 30% greater electrorefractive effect, to counteract the observed underestimation of this effect. Model III assumes a double modulated irradiance of the pump laser to account for the underestimated excess carrier concentration in the substrate. Finally, model IV reduces the layer injection, to counteract the overestimated sensitivity to the active doping concentration in the layer. In particular the latter model assumes that the constant mode of the excess carrier concentration in the substrate $\Delta N_{sub0}$ is equal to $2|\Delta N_{sub1}|$ (lower limit for $\Delta N_{sub0}$). The values used for each of these models can give a good feeling of the impact of the different modeling errors.

FIG. 11(b) compares the depths of the TP and SIMS profiles at a $10^{19}$ cm$^{-3}$ concentration. As already observed in FIG. 9(e), the TP profiles are always deeper than the SIMS profiles. Further, the depths of the SIMS measures it shallower. It can be seen in FIG. 11(b) that, though the depths of the TP profiles vary according to the used model, none of the modified models explains the anti-correlation. The error is therefore seems not correlated to the modeling errors discussed above.

The anti-correlation could be due to an additional modeling error lying in the substrate measurement fitting. As already mentioned, the evolution of $|\Delta R_{ac}^{Profile}|$ in FIG. 9(c) seems to indicate an evolution of the junction depth in agreement with the SIMS profiles. However the trend observed in these data is also partly due to the decrease in the substrate plasma component, as can be observed in FIG. 9(a) and as expected when increasing the Ge PAI dose or energy (increased damage). In other words, the error may be due to a less accurate discrimination between both effects (reduction in substrate plasma component and deeper profile). This may indicate that the variations in $\Delta N_{sub1}$ and $\Delta T_1$ with the energy and dose of the Ge implant are not properly accounted for. Most likely, the assumed homogeneous ambipolar diffusivity and recombination lifetime have to be blamed.

Moving on to FIG. 11(c), it can be seen that the abruptness of the TP profiles is in good agreement with SIMS. Furthermore, it shows only limited sensitivity to the used model. The obtained values are therefore quite robust.

Finally, the comparison of the peak active doping concentrations in FIG. 11(a) shows that $N_0$ is very sensitive to the modeling error. This can easily be explained by the fact that $N_0$ is very sensitive to the modeling error. This can easily be explained by the fact that $N_0$ is fixed by $R_{dc}$ after the depth and abruptness have been determined by $\Delta R_{ac}$. Furthermore, the values of $N_0$ are quite difficult to compare with the $N_{SIMS}^{peak}$ values since the latter assumes crystalline mobility. The impact of modeling error on $N_0$ is complex and in advantageous embodiments can be taken into account when determining depth accuracy.

In conclusion, given the high sensitivity of the depth and active doping concentration of the TP profiles to the modeling error shown in FIG. 11, the discrepancies between the TP and SIMS profiles are believed to be due to modeling errors (including some error that could originate from the fitting of the substrate measurement (impact of Ge implant)).

The involvement of a fitting algorithm in the proposed measurement technique raises the question of the uniqueness of the obtained profile. It should, therefore, primarily be checked that the fitting procedure always converges towards the same values of the three profile parameters $N_0$, $X_{cst}$ and A. Given the discussion above however, it appears obvious that the obtained values of the profile parameters are indeed unique. This can, furthermore, be checked by changing the initial guess values of the three parameters in the fitting algorithm. The variations on the final output values are typically of the order of their respective precisions $\sigma_{N_0}$, $\sigma_{X_{cst}}$, and $\sigma_A$.

Furthermore, it should also be evaluated how dependent the fitting profiles are on the assumption of their shape. To test this dependence, we propose to compare the TP profiles obtained for the samples when respectively assuming an exponentially decaying profile or a profile following the behavior of a complementary error function. FIG. 12 compares the obtained TP profiles for all three samples. While the obtained depths and abruptnesses in the moderately doped regions are independent from the assumed shape, the peak active doping concentrations are significantly impacted by the profile shape.

This behavior can be explained from the theoretical considerations made above. The depth and abruptness are fixed by the $\Delta R_{ac}$ offset curves. Each point of the offset curve being sensitive to a different region of the profile, the moderately doped region of the profile is therefore defined uniquely ($<10^{19}$ cm$^{-3}$). The value of $R_d$, is sensitive not only to the peak doping concentration of the profile but the whole highly doped region ($>10^{19}$ cm$^{-3}$). In other words, the determination of the highly doped regions relies on one single value of $R_{dc}$ which leads to the uncertainty shown in FIG. 12.

Note that, in order to eliminate the ambiguity, the measurement of $\Delta R_{ac}$ with higher substrate injection should be considered.

Above, an example is discussed of the fast non-destructive profile characterization technique based on the combined measurement of $\Delta R_{ac}$ offset curves and $R_{dc}$ according to one embodiment of the present disclosure. The technique has a high precision and is in acceptable agreement with SIMS and SSRM. In advantageous embodiments, modeling errors could be taken into account. Further, the depth and abruptness of the profiles obtained using this technique are unique but the obtained peak active doping concentration depends on the assumed profile shape. A higher pump irradiance alternatively could directly solve this uniqueness problem.

One embodiment also relates to computer-implemented methods for performing at least part of the methods for optically determining a substantially fully activated dopant profile. One embodiment also relate to corresponding computer program products. The methods may be implemented in a computing system. They may be implemented as software, as hardware or as a combination thereof. Such methods may be adapted for being performed on computer in an automated and/or automatic way. In case of implementation or partly implementation as software, such software may be adapted to run on suitable computer or computer platform, based on one or more processors. The software may be adapted for use with any suitable operating system such as for example a Windows operating system or Linux operating system. The computing means may comprise a processing means or processor for processing data. Besides a processor, the computing system furthermore may comprise a memory system including for example ROM or RAM, an output system such as for example a CD-rom or DVD drive or means for outputting information over a network. Conventional computer components such as for example a keyboard, display, pointing device, input and output ports, etc. also may be included. Data transport may be provided based on data busses. The memory of the computing system may comprise a set of instructions, which, when implemented on the computing system, result in implementation of part or all of the standard steps of the methods as set out above and optionally of the optional steps as set out above. The obtained results may be outputted through an output means such as a plotter, printer, and display or as output data in electronic format.

Further aspect of certain embodiments of the present disclosure encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

FIG. 13 shows a block diagram illustrating one embodiment of a system for optically determining a substantially fully activated doping profile. The substantially fully activated doping profile may be characterized by a set of physical parameters. The system 1000 may comprise a measurement module 1010 having a pump laser and a probe laser. The measurement module 1010 is configured to obtain photomodulated reflectance (PMOR) offset curve measurement data and to obtain DC reflectance measurement data of the probe laser. The system 1000 may further comprise a processing module 1020 configured to receive photomodulated reflectance (PMOR) offset curve measurement data, to receive DC reflectance measurement data of the probe laser for a sample and a reference, and to determine, based on the measurement data, values for the set of physical parameters of the doping profile Although systems and methods as disclosed, is embodied in the form of various discrete functional blocks, the system could equally well be embodied in an arrangement in which the functions of any one or more of those blocks or indeed, all of the functions thereof, are realized, for example, by one or more appropriately programmed processors or devices.

It is to be noted that the processor or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. Furthermore, aspects of the invention can be implemented in a computer program product stored in a computer-readable medium for execution by a programmable processor. Method steps of aspects of the invention may be performed by a programmable processor executing instructions to perform functions of those aspects of the invention, e.g., by operating on input data and generating output data. Accordingly, the embodiment includes a computer program product which provides the functionality of any of the methods described above when executed on a computing device. Further, the embodiment includes a data carrier such as for example a CD-ROM or a diskette which stores the computer product in a machine-readable form and which executes at least one of the methods described above when executed on a computing device.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of optically determining a substantially fully activated doping profile, the substantially fully activated doping profile being characterized by a set of physical parameters, the method comprising:

obtaining a sample comprising a fully activated doping profile and a reference;

obtaining photomodulated reflectance (PMOR) offset curve measurement data and DC reflectance measurement data for the sample comprising the fully activated doping profile and for the reference; and determining values for the set of physical parameters of the doping profile based on both the photomodulated reflectance offset curve measurements and the DC reflectance measurements, wherein determining the set of physical parameters of the doping profile comprises determining from the photomodulated reflectance offset curve measurement data on the sample and from the DC reflectance measurement on the sample at least one of a junction depth $X_j$, an active doping concentration $N_{act}$ and a profile abruptness or backside slope $S_{act}$.

2. The method according to claim 1, wherein obtaining photomodulated reflectance offset curve measurement data and DC reflectance measurement data comprises performing a photomodulated reflectance offset curve measurement and a DC reflectance measurement.

3. The method according to claim 1, wherein obtaining photomodulated reflectance offset curve measurement data and DC reflectance measurement data comprises obtaining data recorded using the same measurement setup.

4. The method according to claim 3, wherein the DC reflectance measurement data is DC reflectance of a probe laser of a photomodulated reflectance offset curve measurements used for determining the photomodulated reflectance offset curve measurements.

5. The method according to claim 1, wherein obtaining photomodulated reflectance offset curve measurement data and DC reflectance measurement data comprises obtaining data which is recorded substantially simultaneous.

6. The method according to claim 1, wherein the method comprises selecting a predetermined profile shape for fully activated doping profile defined by the set of physical parameters, wherein determining values for the set of physical parameters comprises determining values for the set of physical parameters defining the predetermined profile shape.

7. The method according to claim 6, wherein the predetermined profile shape is any of the following: part of a Gaussian shape, part of a Lorentzian shape, part of a complementary error function, and a box shape or box-like shape.

8. The method according to claim 1, wherein determining the set of physical parameters of the doping profile comprises determining a surface excess carrier concentration $\Delta N_{sub}$ and excess temperature $\Delta T_{surf}$ from the photomodulated reflectance offset curve measurement data obtained for the reference and determining a reflectance $R_0$ from the DC measurement data obtained for the reference.

9. A non-transitory computer-readable medium having stored therein instructions which, when executed on a processor, performs the method according to claim 1.

10. A system for optically determining a substantially fully activated doping profile, the substantially fully activated doping profile being characterized by a set of physical parameters, the system comprising:

means for obtaining a sample comprising a fully activated doping profile and a reference;

means for obtaining photomodulated reflectance (PMOR) offset curve measurement data and DC reflectance measurement data for the sample comprising the fully activated doping profile and for the reference; and means for determining values for the set of physical parameters of the doping profile based on both the photomodulated reflectance offset curve measurements and the DC reflectance measurements, wherein the determining means further comprises means for determining from the photomodulated reflectance offset curve measurement data on the sample and from the DC reflectance measurement on the sample at least one of a junction depth $X_j$, an active doping concentration $N_{act}$ and a profile abruptness or backside slope $S_{act}$.

* * * * *